United States Patent
Qian et al.

(10) Patent No.: US 8,802,435 B2
(45) Date of Patent: *Aug. 12, 2014

(54) EXTRACELLULAR MATRIX COATED SURFACE FOR CULTURING CELLS

(75) Inventors: Susan X. Qian, Concord, MA (US); Suparna Sanyal, Tewksbury, MA (US)

(73) Assignee: Corning Incorporated, Corning, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 13/547,197

(22) Filed: Jul. 12, 2012

(65) Prior Publication Data

US 2012/0282691 A1  Nov. 8, 2012

Related U.S. Application Data

(62) Division of application No. 11/747,523, filed on May 11, 2007, now Pat. No. 8,241,908.

(60) Provisional application No. 60/747,349, filed on May 16, 2006, provisional application No. 60/817,972, filed on Jun. 30, 2006, provisional application No. 60/817,736, filed on Jun. 30, 2006, provisional application No. 60/883,083, filed on Jan. 2, 2007, provisional application No. 60/886,984, filed on Jan. 29, 2007.

(51) Int. Cl.
*C12N 5/00* (2006.01)
*C12M 1/00* (2006.01)
*C12N 5/0735* (2010.01)

(52) U.S. Cl.
CPC .............. *C12M 23/00* (2013.01); *C12N 5/0606* (2013.01); *C12N 2533/52* (2013.01)
USPC ........................................................ 435/395

(58) Field of Classification Search
None
See application file for complete search history.

(56) References Cited

U.S. PATENT DOCUMENTS

| | | |
|---|---|---|
| 5,234,822 A | 8/1993 | Pereira et al. |
| 5,281,522 A | 1/1994 | Senyei et al. |
| 5,627,037 A | 5/1997 | Ward et al. |
| 5,731,417 A | 3/1998 | Swiderek et al. |
| 6,740,501 B2 | 5/2004 | Mannuzza et al. |
| 7,608,455 B2 | 10/2009 | Wu et al. |

FOREIGN PATENT DOCUMENTS

| | | |
|---|---|---|
| EP | 1 264 878 A2 | 12/2002 |
| WO | WO 01/51616 A2 | 7/2001 |

OTHER PUBLICATIONS

"BD Matrigel Matrix High Concentration" retrieved from http://www.bdbiosciences.com/external_files/d1/doc/mkt_lit/salesSheets/F03G065.pdf.
Smith-Arica, Joseph R. et al.: "Infection efficiency of human and mouse embryonic stem cells using adenoviral and adeno-associated viral vectors", Cloning and Stem Cells, 2003, vol. 5, No. 1, 2003, pp. 51-62.
Parish et al., "A Basement-Membrane Permeability Assay Which Correlates with the Metastatic Potential of Tumor Cells", Int. J. Cancer; 52, 378-383 (1992).
Mallon et al., "Toward xeno-free culture of human embryonic stem cells", 38: 1063-1075 (2006).
CELLCOAT® Protein Coated Cell Culture Vessels, Greiner bio-one, (Jul. 2005).

*Primary Examiner* — Allison Ford
(74) *Attorney, Agent, or Firm* — Hoffmann & Baron, LLP (57) ABSTRACT

A cell culture product is provided for propagating embryonic stem cells, and maintaining their self-renewal and pluripotency characteristics for extended periods of time in culture. The cell culturing product includes a substrate; and a coating thereon deposited from a coating solution. The coating solution includes a mixture of extracellular matrix proteins and an aqueous solvent, wherein the total protein concentration in the coating solution is about 10 μg/ml to about 1 mg/ml.

14 Claims, 2 Drawing Sheets

EXTRACELLULAR MATRIX COATED SURFACE FOR CULTURING CELLS

CROSS-REFERENCE TO RELATED APPLICATIONS

This application is a divisional of U.S. patent application Ser. No. 11/747,523, filed May 11, 2007, now allowed, and claims the benefit of U.S. Provisional Application No. 60/747,349, filed May 16, 2006, U.S. Provisional Application No. 60/817,942, filed Jun. 30, 2006, U.S. Provisional Application No. 60/817,736, filed Jun. 30, 2006, U.S. Provisional Application No. 60/883,083, filed Jan. 2, 2007, and U.S. Provisional Application No. 60/886,984, filed Jan. 29, 2007, the entire contents each of which is incorporated by reference in their entirety herein.

FIELD OF THE INVENTION

The present invention relates generally to the field of cell culturing. More specifically, the invention relates to a substrate coated with an extracellular matrix composition suitable for culturing embryonic stem cells.

BACKGROUND OF THE INVENTION

Embryonic stem cells are characterized as cells with high telomerase activity, infinite capacity for self-renewal, and pluripotency (the ability to differentiate into any cell type represented in the three germ layers, ectoderm, endoderm and mesoderm). As a result, a great deal of hope is associated with the potential application of human embryonic stem (hES) cells in the fields of gene/cell therapy and regenerative medicine.

The first successful derivation of human embryonic stem (hES) cells was reported by Thomson, J. A. et al. (Science (1998) 282:1145-1147). In that study, hES cells were isolated from the inner cell mass of blastocysts and plated onto mitotically inactivated murine embryonic fibroblast (MEF) feeder cells. Initial hES cell derivation and culture has originated from culturing practices developed predominantly for murine ES (mES) cells over the past 25 years. While MEF feeders have proved to be a robust surface for long term cultures of hES cells, this methodology has several limitations. First, there are concerns about potential animal pathogens that could be transferred to the hES cells, making them unsuitable for clinical applications. Second, it is inconvenient and tedious to grow and maintain two cells types. Furthermore, it is difficult to transfect and genetically manipulate the compacted hES cell colonies on feeders. For all these reasons, efforts have been initiated to develop feeder-free conditions for culturing hES cells.

Mouse ES cell research has served as a foundation for furthering our understanding of the mechanism of regulating self-renewal of hES cells. Manipulation of specific signaling regulators has facilitated the development of feeder-free conditions required for propagating undifferentiated hES cells. Recent studies have clearly delineated that hES cells can be grown in the absence of feeders, as long as they are plated on an appropriate extra-cellular matrix (ECM) and cultured in media either conditioned on feeder cells or supplemented with soluble factors.

An extracellular matrix (ECM) is a three-dimensional molecular complex that varies in composition, and may include components such as laminin, fibronectin, collagens and other glycoproteins, hyaluronic acid, proteoglycans, and elastins. Examples of commercially available extracellular matrices include, for example, ECM gel by Sigma-Aldrich or Matrigel™ Matrix by Becton, Dickinson & Company. Matrigel™ Matrix is a reconstituted basement membrane isolated from mouse Engelbreth-Holm-Swarm (EHS) tumor. Matrigel™ matrix is composed predominantly of laminin, collagen IV, entactin and heparan sulfate proteoglycans. Matrigel™ matrix also contains a number of growth factors, such as EGF, IGF-1, PDGF, TGF-$\beta$, VEGF and bFGF.

Prior to the present invention, it was known that hES cells could be propagated in an undifferentiated state on an ECM surface using conditioned media from different types of feeder cells. There are a number of advantages in using an ECM as a feeder-free substrate for culturing hES cells. For instance, DNA, RNA and protein isolation is easier on an ECM surface due to lack of potential contamination from the feeder cells. In addition, genetic manipulation of hES cells requires efficient transfection capabilities. Transfection efficiencies of hES cells grown on a Matrigel surface are improved compared to those grown on feeders. When cultured on BD Matrigel™ Matrix, it was previously shown that hES cells form "monolayer-like" colonies, making individual cells more accessible for penetration with DNA or SiRNA. Although other ECM proteins have also been successfully used for feeder-free cultures, several prior studies have suggested that a combination of ECM proteins is required to perform as well as Matrigel™ Moreover, purified proteins are generally more expensive and not as well tested for long-term performance as Matrigel™.

Despite the wide acceptance of Matrigel™ as a viable substrate for long term feeder-free culture of hES cells, it has one key limitation. Since Matrigel™ is derived from the EHS tumor, lot-to-lot variability in protein concentration and composition is inherent. In order to limit the amount of time researchers spend today pre-screening lots of Matrigel™ and coating substrates on a weekly basis, it would be of benefit to provide a stable, ready-to-use substrate coated with an optimal ECM composition for ES culture. Preferably, this culturing system would provide lot-to-lot consistency, which is needed for standardized ES cultures.

SUMMARY OF THE INVENTION

The present invention provides culturing apparatuses and methods using such culturing apparatuses for the stable, consistent propagation of pluripotent embryonic stem cells in a substantially undifferentiated state without utilizing a feeder layer to support the growth of the cells, wherein the stem cells are propagated on an extracellular matrix (ECM) coated surface. Surprisingly, it has been discovered that, in order to propagate and maintain embryonic stem cell cultures in an undifferentiated state, it is not necessary to provide an extracellular matrix coating in an amount sufficient to produce a 3D matrix for the cell. Rather, the extracellular matrix coating only needs to be adsorbed by or bound to the cell culturing surface in a minimal solution concentration sufficient to provide extracellular matrix proteins at a saturated level in a proper conformation. As defined herein, the term "saturation level" means that adding more ECM proteins in the coating solution will not increase the amount of ECM proteins absorbed on the surface after washing. The saturation level can be measured by different means, including by both ELISA and the number of colonies.

The present invention provides an improved extracellular matrix (ECM) coated culture surface for propagating embryonic stem cells, including hES cells, and for maintaining their self-renewal and pluripotency characteristics for extended periods of time in culture.

In particular, the present invention provides a cell culture product including a substrate; and an extracellular matrix coating thereon, wherein the coating is adsorbed or bound to at least one surface of the substrate in a minimal solution concentration sufficient to provide extracellular matrix proteins at a saturation level on the substrate surface. In some embodiments, the total amount of extracellular matrix protein adsorbed by or bound the substrate surface is from about 200 ng/cm$^2$ to about 650 ng/cm$^2$.

In particular, the present invention provides a cell culture product including a substrate; and a coating thereon. The coating includes at least one extracellular matrix protein and can be formed by a coating solution including the extracellular matrix protein and an aqueous solvent, wherein the total protein composition in the coating solution is about 10 µg/ml to about 1 mg/ml or higher. In situations where the concentration of the total protein in the coating solution exceeds 1 mg/ml, it is possible that the total protein may exceed the protein binding capacity of the surface. However, in this instance, any unbound protein may be washed off the surface.

The invention further provides a cell culture product including a substrate; and a coating thereon deposited from a coating solution. The coating solution includes a mixture of extracellular matrix proteins and an aqueous solvent, wherein the total protein concentration in the coating solution is about 10 µg/ml to about 1 mg/ml or higher.

The cell culture product of the invention can be characterized by the density of extracellular matrix protein(s) adsorbed to the coated surface relative the density of extracellular matrix protein(s) adsorbed to an uncoated, but otherwise identical control surface. In particular, the present invention provides a cell culture product that includes a substrate material defining a surface, and a coating deposited on the surface of the substrate, in which the coating includes at least one extracellular matrix protein selected from the following: collagen, laminin, entactin, and heparan sulfate proteoglycans (HSPG), and the density of the extracellular matrix protein adsorbed to the surface is such that the ratio of the optical density (OD) from an ELISA assay performed on the coated cell culture product compared to an uncoated control cell culture product is greater than about 4.0 when the ODs are obtained by an ELISA. In some embodiments, the OD from an ELISA performed on the coated cell culture product compared to an uncoated cell culture product is about 4 to about 5. The ELISA assay includes (a) washing the surface to remove non-adsorbed proteins; (b) contacting the surface with an excess of a primary antibody directed against the extracellular matrix protein; (c) washing the surface to remove unbound primary antibody directed against the extracellular matrix protein; (d) contacting the surface with an excess of a secondary antibody directed against the primary antibody and conjugated to horseradish peroxidase enzyme; (e) washing the surface to remove unbound secondary antibody; (f) contacting the surface with a solution of tetramethylbenzidine (TMB) substrate to form a reaction mixture; (g) adding an acidic stop solution to the reaction mixture following oxidation of the TMB substrate, as indicated by a color change in the reaction mixture; (h) measuring the OD at a wavelength of 450 nm.

The present inventors have discovered that between about 0.6 µg/cm$^2$ to about 6.0 µg/cm$^2$ of extracellular matrix components in the coating solution is sufficient to provide a cell culturing apparatus sufficient to propagate embryonic stem cells. In some embodiments, the amount of protein bound to a surface, such as a polystyrene surface, may range from about 200 ng/cm$^2$ to about 650 ng/cm$^2$, depending on the surface treatment and the properties of the ECM protein(s).

The extracellular matrix coating can be dried, providing a consistent surface containing extracellular matrix components. In one embodiment, the apparatus is capable of storage at room temperature for an extended period of time. In one embodiment, the apparatus can be stored at room temperature for at least two weeks.

The culturing apparatus of the present invention provides for less aggregation of protein complexes on the coated surfaces than seen with other protocols, and a higher amount of protein adsorbed to the surface of the culturing apparatus. Combined with the ability of the bound extracellular matrix components to be washed, thus removing unbound protein, and dried, culturing apparatuses of the present invention provide a more consistent lot-to-lot surface for propagating embryonic stem cells.

The present invention also provides a culturing apparatus for culturing pluripotent embryonic stem cells including: i) a container suitable for culturing cells; ii) a fixed concentration of extracellular matrix components, wherein the extracellular matrix is in a dried state on at least one surface of the container; and optionally, iii) an agent suitable for stabilizing the extracellular matrix in a dried state.

Also provided are methods of preparing the cell culture products/apparatuses of this invention. In some embodiments, the method includes applying an extracellular matrix coating solution to a surface of a substrate, wherein the total protein concentration in the coating solution is about 10 µg/ml to about 1 mg/ml. The method also includes incubating the coating solution on the substrate surface; removing the incubated coating solution from the substrate; and washing the substrate after the removing step. Finally, the method includes drying the washed substrate; and sterilizing the dried substrate.

In other embodiments, the culturing method includes the steps of a) applying a first liquid solution containing an extracellular matrix in a fixed concentration to a container suitable for cell culturing, wherein the extracellular matrix includes at least laminin; b) incubating the container for a period of time sufficient to allow binding of the extracellular matrix with the container; c) removing said first solution from the container; d) washing the container to remove any of the first solution remaining in the container; and e) drying the container. In some embodiments, the extracellular matrix includes a mixture of laminins. For example, eleven isoforms of laminin have been proposed, and a suitable mixture may include two or more of these isoforms. In some further embodiments, the extracellular matrix includes a mixture of laminin and entactin. In still further embodiments, the extracellular matrix includes a mixture of laminin and collagen IV.

Further provided are methods of culturing embryonic stem cells. In some embodiments, the method includes providing a cell culture product including a substrate; and a coating thereon deposited from a coating solution. The coating solution includes a mixture of extracellular matrix proteins and an aqueous solvent, the total protein concentration in the coating solution being about 10 µg/ml to about 1 mg/ml. The culturing method also includes adding a suspension of embryonic stem cells and media to the cell culture product; and incubating the embryonic stem cells at 5% $CO_2$ in humidified air at 37° C. to produce undifferentiated colonies for embryonic stem cell expansion.

In some other embodiments, the method for propagating embryonic stem cells includes the step of a) providing an apparatus for propagating pluripotent embryonic stem cells that includes a container suitable for culturing cells; and an extracellular matrix in a fixed concentration; wherein the extracellular matrix includes at least laminin; and wherein the extracellular matrix is in a dried state on at least one surface of the container. This method further includes the steps of b) adding a cell culture medium that has been previously conditioned by an appropriate feeder culture to the container; and c) adding undifferentiated pluripotent embryonic stem cells to the container. Moreover, the method includes the step of d) incubating the container including the pluripotent embryonic stem cells under a suitable condition to allow for the propagation of the pluripotent embryonic stem cells.

DETAILED DESCRIPTION OF THE INVENTION

Culturing Apparatus

An improved coated culture surface is provided herein for propagating cells, including embryonic stem cells, and particularly hES cells, and maintaining their self-renewal and pluripotency characteristics for extended periods of time in culture. Since Matrigel™ is derived from the EHS tumor, lot-to-lot variability in protein concentration and composition is inherent. The present invention eliminates the need for researchers to spend exhaustive amounts of time pre-screening lots of Matrigel™ and coating substrates on a weekly basis. In particular, the present invention provides a stable, ready-to-use substrate coated with an improved ECM composition for ES culture. This cell culture product provides lot-to-lot consistency, which is needed for standardized ES cultures. It is noted that the terms "cell culture product", "culturing apparatus" and the like may be used interchangeably herein.

In some embodiments, the present invention is directed to a cell culture product including a substrate; and a coating thereon deposited from a coating solution. The coating solution includes a mixture of extracellular matrix proteins and an aqueous solvent, wherein the total protein concentration in the coating solution is about 10 µg/ml to about 1 mg/ml. In some preferred embodiments, the total protein concentration in the coating solution is about 30 µg/ml to about 300 µg/ml. In more preferred embodiments, the total protein concentration in the coating solution is about 30 µg/ml to about 200 µg/ml.

The coating preferably includes a mixture of extracellular matrix proteins. In some embodiments, the coating includes a mixture of a laminin and at least one other extracellular matrix component. In some embodiments, the mixture includes more than one laminin isoform. In some other embodiments, the mixture includes at least one laminin and entactin. In further embodiments, the mixture includes at least one laminin and collagen IV.

Non-limiting examples of extra-cellular matrix molecules useful in the present invention include fibronectin, vitronectin, collagens, laminin, elastin, various proteoglycans, glycosaminoglycans and the like. The extra-cellular matrix components are suspended in a liquid solution and applied to a container suitable for culturing cells. In one embodiment, the extra-cellular matrix components are composed of molecules that form a basement membrane.

As described above, in some embodiments, the coating includes a mixture of a laminin and at least one other extracellular matrix component. In some embodiments, the coating includes a mixture of laminins.

In some other embodiments, the coating includes a laminin/collagen IV mixture. A suitable weight ratio for the laminin/type IV collagen mixture is about 1.5 to about 2.5. In one embodiment, this coating further includes one or more of the following components: entactin, heparan sulfate proteoglycans (HSPG) and growth factors. In some embodiments, the coating includes a laminin/entactin mixture.

In still further embodiments, the coating includes a laminin/entactin mixture. For example, a suitable coating solution may be prepared by diluting BD laminin/entactin complex (Becton, Dickinson & Co.; catalog no. 354259) A suitable weight ratio for the laminin/entactin complex is about 5 to about 9. In one embodiment, this coating may further include a component selected from the following: type IV collagen, heparan sulfate proteoglycans (HSPG), growth factors and combinations thereof.

In further embodiments, the extracellular matrix coating includes at least laminin, collagen IV and entactin. In one embodiment, the laminin component is present at about 40% to about 70% of the extracellular matrix components. In one embodiment, the collagen IV component is present at about 20% to about 40% of the extracellular matrix components. In one embodiment, the entactin component includes between about 3% to about 15% of the extracellular matrix components. In one embodiment, the extracellular matrix components further include heparin sulfate proteoglycans, growth factors, such as PDGF, EGF, and TGF-β and matrix metalloproteinases, or a combination thereof.

In some embodiments, the coating includes at least laminin, collagen IV, entactin and heparan sulfate proteoglycans. For example, a coating solution may be prepared by diluting a basement membrane protein extract, such as BD Matrigel™ Basement Membrane Matrix (Becton, Dickinson & Co., Bedford, Mass.). A suitable weight ratio for Matrigel™ is about 5 to about 9. This protein extract contains, in parts by weight, about 50-85% laminin, 5-30% collagen IV, 1-10% entactin (nidogen) and 1-10% heparan sulfate proteoglycans. For example, in one embodiment, the coating solution may be prepared by diluting a BD Matrigel™ Matrix including about 56% laminin, about 31% collagen IV, and about 8% entactin, as well as heparan sulfate proteoglycans, growth factors and matrix metalloproteinases.

In one embodiment, the extracellular matrix coating includes about 61% laminin, about 30% collagen IV, and about 7% entactin, as well as heparan sulfate proteoglycans, growth factors, and matrix metalloproteinases. For example, the coating solution may be prepared from the commercially available product Growth Factor Reduced BD Matrigel™ (Becton, Dickinson & Co., Bedford, Mass.), which includes laminin, collagen IV and entactin in amounts of about 61%, 30% and 7%, respectively.

In one embodiment, the extracellular matrix includes an extracellular matrix derived from a mammalian placental membrane. In one embodiment, the placental membrane is a human placental membrane.

The concentration of extracellular matrix components suspended in the coating solution and applied to surface suitable for culturing cells provides an optimal extracellular matrix layer on the surface that allows for consistent performance of the cell culture surface in maintaining embryonic cells in an undifferentiated state. The present inventors have found that, if the concentration of the extracellular matrix components on the surface is too low, then embryonic stem cell propagating colony numbers may be reduced. If the concentration of the extracellular matrix components in the solution is too high, then the extracellular matrix components may precipitate in solution, creating a non-uniform matrix with less than a saturated level of protein on the surface and potentially affecting the ability of the embryonic stem cells to propagate.

In one embodiment, the cell culture apparatus includes a thin layer of the extracellular matrix components on a surface thereof. In one embodiment, the extracellular matrix components are present in a dried state on at least one surface of a container.

In one embodiment of the present invention, the extracellular matrix components are applied to a container in a concentration of between about 10 µg/mL and about 500 µg/mL. In one embodiment, the extracellular components are applied to a container in a concentration of between about 30 µg/mL and about 300 µg/mL. In a particular embodiment, the extracellular components are applied to a container in a concentration of about 100 µg/mL.

The amount of liquid solution containing a fixed concentration of extracellular matrix components applied to the container may vary depending on the type and size of the container and the concentration of the extracellular components in the liquid solution. In one embodiment, between about 0.05 mLs and about 0.5 mLs of liquid solution are applied per $cm^2$ of container area ($mL/cm^2$). In one embodiment, between about 0.1 $mL/cm^2$ and about 0.2 $mL/cm^2$ are applied to the container.

In one embodiment, the solution is applied to provide for between about 0.1 µg of extracellular matrix components per $cm^2$ of container area and about 10 µg of extracellular matrix components per $cm^2$ of container area ($\mu g/cm^2$). In one embodiment, the solution is applied to the container to provide for between about 0.6 $\mu g/cm^2$ and 6.0 $\mu g/cm^2$.

In some embodiments, the coating is present on the substrate in a dry state. The resulting product is more stable if the coating is dried. Moreover, it is preferred that the cell culture product is prepared by a coating process, which includes washing of unbound protein. This permits more consistency from lot-to-lot, since the uncontrolled amount of unbound protein is washed away. The final coated substrate is useful for culturing cells, including ES cells, and maintaining them in an undifferentiated state during cell expansion.

In one embodiment, the coating on the substrate is further formed from a blocking solution. The blocking solution includes at least one blocking agent and an aqueous solvent, such as a buffer or cell culture medium. In some embodiments, the blocking agent may be gelatin, sucrose, trehalose or a combination of these. It is noted that the term "blocking agent" may be used interchangeably herein with the term "stabilizing agent". Preferably, the blocking agent is present in the blocking solution in an amount of about 0.1 to about 5.0% w/v.

The present inventors have found, for example, that blocking of the substrate surface with a blocking solution including at least one blocking agent, such as sucrose, increased the stability of the dried coating during an accelerated aging test at higher temperatures. For example, the present inventors have found that a blocking/stabilizing agent, such as sucrose, extended the ability of the cell culture product/culturing apparatus to be stored at room temperature for an extended time without significant degradation of the extracellular matrix components. In one embodiment, the cell culture product may be stored for at least two weeks at room temperature. This saves freezer, refrigerator or cold room space, for example. Further, because the cell culture product can be stored at room temperature, time is also saved because the cell culture product need not be thawed prior to use.

In one embodiment of the present invention, a cell culturing apparatus containing an extracellular matrix coating in a dried state may also contain a stabilizing agent that allows the cell culturing apparatus to be stored at room temperature for an extended period of time. In particular, the present invention provides a culturing apparatus for culturing pluripotent embryonic stem cells including: i) a container suitable for culturing cells; ii) a fixed concentration of extracellular matrix components, wherein the extracellular matrix is in a dried state on at least one surface of the container; and optionally, ii) an agent suitable for stabilizing the extra-cellular matrix in a dried state. It is believed that the addition of a stabilizing agent prevents significant degradation of the extracellular matrix components in the coating.

The stabilizing agent can be applied to at least one surface of a container, such as a cell culture plate or flask, at a suitable concentration such that the degradation of the extracellular matrix components in the coating is prevented or inhibited. In one embodiment, the stabilizing agent is applied at a concentration of about 0.1% to about 5.0% w/v. In one embodiment, the stabilizing agent is applied at a concentration of about 1.25% w/v. The concentration may be measured in terms of the weight of the stabilizing agent per unit of volume of a liquid solution. In exemplary embodiments, the weight of the stabilizing agent may be measured in grams, and the volume of the liquid solution may be measured in milliliters.

Any stabilizing agent that is capable of preventing the degradation of the extracellular matrix while not interfering with the propagation of an embryonic stem cell can be used in the present invention. In one embodiment, the stabilizing agent is selected from the following: sucrose, trehalose and combinations thereof. In one embodiment, the stabilizing agent is sucrose.

The aqueous solvent used to prepare the coating and blocking solutions may be a buffer, such as PBS, or a cell culture media, for example. In some embodiments, DMEM, KO/DMEM, RPMI or other cell culture mediums known in the art, are suitable for use as the aqueous solvent used to prepare the coating solution. Suitable aqueous solvent diluents can include any cell culture medium, which provides a condition that is compatible with cell culture, and preferably maintains ES cells in a self-renewing and an undifferentiated state until directed into a particular cell type in vitro. Such media may be obtained commercially, for example, from Invitrogen Corporation (Carlsbad, Calif.) or Sigma-Aldrich (St. Louis, Mo.).

In some embodiments, the coating solution has a pH of between about 7.0 to about 8.5. The pH may be maintained with any buffering component capable of maintaining the coating solution within the pH range of about 7.0 to 8.5. Potential buffer systems in this range include, but are not limited to, diethanolamine, triethanolamine, (1,3-bis(tris[Hydroxymethyl]methylamino)propane); 3-[N,N-bis(2-Hydroxyethyl)amino]-2-hydroxypropanesulfonic acid: DIPSO; (N-[2-Hydroxyethyl]piperazine-N'-[-4-butanesulfonic acid] HEPBS); (N-(4-(2-hydroxyethyl-1-piperazineethanesulfonic acid: HEPES); 3-(N-Morpholino)butane sulfonic acid: MOBS); (piperazine-N,N'-bis[2-hydroxypropanesulfonic acid: POPSO); (N-tris(Hydroxymethyl)methyl-3-aminopropanesulfonic acid: TAPS; 3-(N-tris[Hydroxymethyl]methylamino)-2-hydroxypropanesulfonic acid: TAPSO); (N-tris(Hydroxymethyl)methyl-2-aminoethanesulfonic acid: TES; (N-tris(Hydroxymethyl)methylglycine:

Tricine; N-ethylmorpholine, dimethylleucylglycine, sodium 5:5-diethyl barbituate and 2 amino, 2 methyl-1:3 propanediol.

In some further embodiments, the coating solution may have an acidic pH. For example, collagens are typically coated in acidic acid at a low pH. The acidic acid will evaporate during drying of the coating. With respect to collagens, an acidic pH is preferred for the coating solution because collagen forms a gel at higher pHs.

In one embodiment, the ECM-coating of the cell culture product is formed from a diluted basement membrane protein extract. As defined herein, the "extracellular matrix" (of which the basement membrane is a specific type), is a material produced by cells and secreted into the surrounding medium. It is noted that the term "extracellular matrix" may be used interchangeably herein with the term "basement membrane". The extracellular matrix can be secreted by cells to form an interstitial basement membrane that forms the framework to which cells are attached. The basement membrane separates cells from mesenchymal connective tissue and provides spatial orientation and the stability required for the growth and differentiation of cells. Extracellular matrix molecules or basement membranes have also been implicated in the sequestration, storage and presentation of growth factors to tissues.

The basement membrane includes various components. The basement membrane is a specific type of extra-cellular matrix and is composed primarily of laminin and type IV collagen. Its major component is laminin, followed by collagen IV, heparan sulfate proteoglycans and entactin.

Extracellular matrix molecules or basement membranes are known in the art and are commercially available. For example, an extracellular matrix from EHS mouse sarcoma tumor is available as Matrigel® (Becton, Dickinson & Co., Medford, Mass.), ECM gel (Sigma-Aldrich Co., St. Louis, Mo.), and Cultrex™ (Trevigen, Gaithersburg, Md.). Further suitable ECM molecules include, for example, laminin/entactin complex (Becton, Dickinson & Co.)

The term "extracellular matrix" is art recognized. Its components include one or more of the following proteins: fibronectin, laminin, vitronectin, tenascin, entactin, thrombospondin, elastin, gelatin, collagen, fibrillin, merosin, anchorin, chondronectin, link protein, bone sialoprotein, osteocalcin, osteopontin, epinectin, hyaluronectin, undulin, epiligrin, and kalinin. Other extracellular matrix molecules are described in Kleinman et al., *J. Biometer. Sci. Polymer Edn.*, 5: 1-11, (1993), herein incorporated by reference. It is intended that the term "extracellular matrix" encompass a presently unknown extracellular matrix that may be discovered in the future, since its characterization as an extracellular matrix will be readily determinable by persons skilled in the art.

A well-known Basement Membrane Matrix extracted from the Englebreth-Holm-Swarm mouse tumor, is sold under the brand name Matrigel™. This mouse tumor is rich in basement membrane proteins. The major matrix components are laminin, collagen IV, entactin and heparan sulfate proteoglycan and also contains growth factors, matrix metalloproteinases (MMPs [collagenases]), and other proteinases (plasminogen activators), as well as several undefined compounds. At room temperature, Matrigel™ Matrix gels to form reconstituted basement membrane and is similar in its structure, composition, physical property and ability to retain functional characteristics typical of basement membranes in vivo.

As described above, the coating solutions used to prepare the cell culture products of the present invention may include a mixture of extracellular matrix proteins. In one desired embodiment, the coating solution is obtained via dilution of an extracellular matrix, which is provided as a basement membrane protein extract, such as that disclosed in U.S. Pat. No. 4,829,000, the entire contents of which are hereby incorporated by reference. This protein extract contains in parts by weight about 50-85% laminin, 5-30% collagen IV, 1-10% entactin (nidogen) and 1-10% heparan sulfate proteoglycans. This protein extract is capable of polymerizing into a rigid stable gel (i.e., a 3-dimensional matrix) on heating. In particular, when incubated at temperatures from about 15-40° C., preferably from about 22-37° C., for a sufficient time, the extracellular matrix proteins polymerize. The proteins can remain in soluble form by maintaining a temperature of the composition lower than this range. Preferably, the extracellular matrix stock composition is maintained at −20° C., thawed and kept at 4° C. prior to being diluted with aqueous solvent to prepare the coating solution.

The coating solutions used to prepare the cell culture products of the present invention can include various components, which can affect the accessibility of growth factors in the coating to cells and/or which assist in cell adhesion and/or which affect the structure of the proteins in the coating. These components may include, but are not limited to, salts, diluents, heparan sulfate proteoglycans and/or neutralization antibodies.

The neutralization antibodies which are suitable include those compounds which affect the growth factor inherent in the extracellular matrix by titrating out the growth factor or blocking their effectiveness. Suitable neutralization antibodies may include, but are not limited to, antibodies against one of the following: TGF-β, EGF, VEGF, PDGF, bFGF and IGF-1.

A wide variety of other materials may be included in the coating on the substrate. These include, but are not limited to, cells, antibodies, enzymes, receptors, growth factors, additional components of the extracellular matrix, cytokines, hormones and drugs. In some embodiments, the extracellular matrix proteins can bind to these materials. These biologically active materials, if present, can be readily available to the cultured cells to moderate or regulate their properties or behavior.

Substrates for conventional cell culture research include plastic, glass, and micro porous filters (e.g., cellulosic, nylon, glass fiber, polystyrene, polyester, and polycarbonate). Substrates for bio-reactors used in batch or continuous cell culture or in genetic engineering include hollow fiber tubes or micro carrier beads. Substrates for vascular or bone grafts include materials such as polytetrafluoroethylene (Teflon®), ceramics and related polymeric materials. Any of these substrates are suitable for use in the present invention.

In some embodiments, the substrate/container may be made of any suitable material capable of allowing the extracellular matrix components to adsorb or bind to at least one surface of the substrate or container. Such materials may include the following: cellulose, polystyrene, polycarbonate, polytetrafluoroethylene, nylon, glass, polyethyleneterephthalate, polymethylpentane, polypropylene, polyethylene and combinations thereof. Other materials that may be employed include Permanox®, polyester, polyamide, polyimide, and silica-based materials, including glass containers and the like. Combinations of any of the aforementioned materials may also be used. These materials may be porous or non-porous.

Preferred substrate configurations/containers contemplated by the present invention include multiwell plates (such as 6-well and 24-well plates), dishes (such as petri dishes), culture flasks, roller bottles, including roller bottles, tubes, bioreactors and the like.

Methods of Preparation

The present invention provides a method of preparing a stable, ready-to-use cell-culture product. This method includes applying an extracellular matrix coating solution to a surface of a substrate, wherein the total protein concentration in the coating solution is about 10 µg/ml to about 1 mg/ml. The method also includes incubating the coating solution on the substrate surface; removing the incubated coating solution from the substrate; and washing the substrate after the removing step. Finally, the method includes drying the washed substrate; and sterilizing the dried substrate. A suitable substrate to which the coating is applied may be selected from those described above, for example.

In some embodiments, the washing step(s) includes washing the substrate with distilled water, a buffer or a culture medium. In other embodiments, the washing step(s) includes washing the substrate with a blocking solution. For example, the washing step used to prepare the cell culture product may employ a blocking solution, whereby the wells are effectively both washed and blocked at the same time.

As described above, the method of preparing the cell culture product/cell culturing apparatus may further include blocking the surface of the substrate after the removing step and prior to or during the washing step with a blocking solution including at least one blocking agent and an aqueous solvent. The blocking agent may be selected from, but is not limited to, gelatin, sucrose, trehalose and combinations thereof. The blocking step was found to increase the stability of the surface during an accelerated aging test at higher temperatures, as described in further detail below. It may be possible to perform the blocking step prior to the removing step and/or to separate the blocking step into multiple steps conducted before and after the removing step.

In one embodiment, the present invention provides for a method of preparing the cell culturing apparatus which includes the steps of:
i) applying a first liquid solution containing extracellular matrix (ECM) components in a fixed concentration to a container suitable for cell culturing,
ii) incubating the container containing the first liquid solution for a sufficient period of time to allow adsorption or binding of the extracellular matrix (ECM) components to the container;
iii) removing the first liquid solution from the container;
iv) washing the container to remove any residual first liquid solution;
v) optionally applying a second liquid solution containing a composition suitable for stabilizing the extracellular matrix;
vi) optionally removing the second liquid solution containing the composition suitable for stabilizing the extracellular matrix,
vii) optionally washing the container to remove any residual second liquid solution; and
viii) drying the container.

A liquid solution including the extracellular matrix components can be incubated on at least one surface of a container, such as a flask or cell culture plate, at a temperature and time period sufficient to allow adsorption of the extra-cellular matrix components to the container surface. For example, the container can be incubated at room temperature from about 1 to about 4 hours to ensure adsorption. Alternatively, the container can be incubated at 4° C. overnight.

The container can be dried in any suitable manner for a suitable amount of time. In one embodiment, the container is dried in a drying oven with vacuum at room temperature. In one embodiment, the container is dried in a drying oven at room temperature for at least 16 hours.

After the culturing apparatus has been dried, it can optionally be sterilized. In one embodiment, the apparatus is sterilized using ultra-violet (UV) light.

The coating procedure is generally performed as follows. Approximately 0.5 to 2.0 ml of the coating solution (desirably at about 4° C.) is applied to a well in a 6-well multiwell plate; about 0.25 to 1.0 ml is applied to a well in a 24-well multiwell plate; and about 50 µl to 100 µl is applied to a well in a 96-well plate. Furthermore, about 0.5 to 2.0 ml is applied to a 35 mm dish, 0.5 to 4.0 ml is applied to a 60 mm dish and 2.0 to 12.0 ml is applied to a 100 mm dish.

After application, the coating solution is incubated to permit adsorption of the extracellular matrix proteins in the solution to the substrate surface. In particular, coated substrates are desirably incubated at temperatures from about 22° C. to about 30° C., and for a period of time of about 30 minutes to about 4 hours to permit adsorption of the proteins to the substrate surface. The coating solution is thereafter removed (e.g., by aspiration), and the coated substrate is washed with either an aqueous solvent (e.g., buffer, ddH$_2$O, culture media) to remove unbound proteins. Use of a blocking solution, as described above, increases the stability of the coated substrate.

In preferred embodiments, the coating is allowed to dry on the substrate. This may be accomplished by drying at a temperature in the range of 22° C. to about 30° C. and desirably at a relative humidity of 40-60%. The present inventors have found that such drying improves the stability of the product. The dried substrate may be sterilized, for example, by UV sterilization. Thereafter, the sterilized, dried substrate may be packaged in moisture-resistant packaging. If desired, the packaged, dried substrate may be stored at −20° C., and then thawed prior to use.

The dried substrate may optionally be rehydrated with cell culture media or another sterile medium (e.g., sterile water) prior to adding the cells. For example, the dried substrate may be rehydrated with a rehydration solution, such a cell culture media, for about 2 minutes to about 2 hours at room temperature. The rehydration solution can then be removed just prior to use. Alternatively, media may be added in order to rehydrate the dried substrate, and then a cell suspension may be added to the media about 2 minutes to about 2 hours later.

Methods of Use

The present invention allows for the growth of the embryonic stem cells in feeder-free cultures. This cell growth may be supported using a medium conditioned by cultures of feeder cells, such as mEFs or other media formulations and an extracellular matrix coating.

As described above, lot-to-lot variability in protein concentration and composition is inherent in matrical gels, such as Matrigel™, which is derived from the EHS tumor. The present invention provides a stable, ready-to-use substrate coated with an optimal ECM composition for ES culture. This cell culture apparatus/product provides lot-to-lot consistency, which is needed for standardized ES cultures.

In particular, a cell culture apparatus according to the present invention permits the consistent propagation of embryonic stem cells in an undifferentiated state. The extracellular matrix coating on the cell culture apparatus is preferably present in a dried state, thereby making the resulting product more stable. Also, the extracellular matrix coating preferably includes a stabilizing/blocking agent, such as sucrose. The present inventors have found that the stability of the dried coating is increased by including a stabilizing/blocking agent in the coating. Moreover, it is preferred that the cell culture product is washed free of unbound protein. This permits more consistency from lot-to-lot, since the uncontrolled amount of unbound protein is washed away.

The compositions and cell culture products/apparatuses of the present invention can be used in various applications, including culturing of ES cells. The improved ECM-coated cell culture surface was found by the present inventors to be useful for maintaining the self-renewal and pluripotency characteristics of the ES cells for extended periods of time. Moreover, cell differentiation of ES cells into a particular cell type, which may be directed in specific ways, such as by adding growth factors to the culture medium in which the ES cells are growing, can be studied using the inventive compositions.

Cell culture products according to the present invention are capable of maintaining and propagating embryonic stem cells, including embryonic stem cells from primates, such as humans, in an undifferentiated state. In some embodiments, the ES cells are human ES cells. For example, human ES cells include, but are not limited to, the following cell lines: H1, H7, H9, and H14, for example. These cell lines are available, for example, from WiCell Research Institute, Madison, Wis. and American Type Culture Collection (ATCC), Manassas, Va. In other embodiments, the ES cells are mouse ES cells, examples of which and suppliers of which are well known in the art.

In one embodiment, the method of culturing embryonic stem cells includes providing a cell culture product of the invention including a substrate; and a coating thereon deposited from a coating solution. The coating solution includes a mixture of extracellular matrix proteins and an aqueous solvent, the total protein concentration in the coating solution being about 10 µg/ml to about 1 mg/ml. The culturing method also includes adding a suspension of embryonic stem cells and media to the cell culture product; and incubating the embryonic stem cells at 5% $CO_2$ in humidified air at 37° C. to produce undifferentiated colonies for embryonic stem cell expansion.

In some embodiments, the method of culturing further includes the step of thawing the cell culture product, which may be stored at −20 C, prior to use. In other embodiments, the culturing method may include the step of hydrating the cell culture product with cell culture medium prior to adding the suspension of embryonic stem cells.

In one embodiment, a method for propagating pluripotent embryonic stem cells in an undifferentiated state includes the steps of:
  a) providing a culturing apparatus formed by the steps including:
    i) applying a first liquid solution containing extracellular matrix (ECM) components in a fixed concentration to a container suitable for cell culturing,
    ii) incubating the container containing the first liquid solution for a sufficient period of time to allow adsorption or binding of the extracellular matrix (ECM) components to the container;
    iii) removing the first liquid solution from the container;
    iv) washing the container to remove any residual first liquid solution;
    v) optionally applying a second liquid solution containing a composition suitable for stabilizing the extracellular matrix;
    vi) optionally removing the second liquid solution containing the composition suitable for stabilizing the extracellular matrix,
    vii) optionally washing the container to remove any residual second liquid solution; and
    viii) drying the container;
  b) adding a suitable cell culture medium that has been previously conditioned by an appropriate feeder cell culture to the container;
  c) adding a suitable concentration of undifferentiated pluripotent embryonic stem cells to the container; and
  d) incubating at a suitable condition to allow for the propagation of the pluripotent embryonic stem cells.

In one embodiment, steps b) and c) above can be performed in a reverse manner, wherein step c) is performed before step b).

In some embodiments, the media used to culture the ES cells is a conditioned or defined cell culture media. In one embodiment, the media is MEF-conditioned medium supplemented with basic fibroblast growth factor (bFGF). The bFGF may be present in an amount of about 4 to about 20 ng/ml in the media. It is noted, however, that the method of culturing is not limited to this culture medium. For example, a number of media have previously been shown to be compatible with culturing ES cells on Matrigel™-coated surfaces. For example, HEF1-conditioned media (Xu, et al. (2004) Stem Cells, 22: 972-980), HES-df-conditioned media (Stojkovic, et al. (2005) Stem Cells, 23:306-314), K-VitroHES media (Sjögren-Jansson, et al. (2005) Developmental Dynamics, 233: 1304-1314), and TesSR1 media including 100 ng/ml bFGF (Ludwig, et al. (2006) Nature Biotechnology, Brief Communications, January 2006) were previously found to be useful in this regard.

By way of illustration, conditioned medium can be prepared by culturing irradiated or mitomycin C-inactivated primary mouse embryonic fibroblasts in a serum replacement medium such as, for example, DMEM, K/O DMEM, or DMEM/F12 containing 4 ng/mL basic fibroblast growth factor (bFGF). The culture supernatant is typically harvested after 1 day at 37° C., and supplemented with additional growth factors, including βFGF. More specifically, feeder-free culture, suitable base media can be made from the following components: Dulbecco's modified Eagle's medium (DMEM), Gibco #11965-092; Knockout Dulbecco's modified Eagle's medium (KO DMEM), Gibco #10829-018; Ham's F12/50% DMEM basal medium; 200 mM L-glutamine, Gibco #15039-027; non-essential amino acid solution, Gibco 11140-050; β-mercaptoethanol, Sigma #M7522; human recombinant basic fibroblast growth factor (bFGF), Gibco #13256-029. Exemplary serum-containing ES medium is made with 80% DMEM (typically KO DMEM), 20% defined fetal bovine serum (FBS) not heat inactivated, 1% non-essential amino acids, 1 mM L-glutamine, and 0.1 mM p-mercaptoethanol. The medium is filtered and stored at 4° C. for no longer than 2 weeks. Serum-free ES medium is made with 80% KO DMEM, 20% serum replacement, 1% non-essential amino acids, 1 mM L-glutamine, and 0.1 mM β-mercaptoethanol. Not all serum replacements work; an effective serum replacement is Gibco #10828-028 (proprietary formula; product obtainable from the manufacturer). The medium is filtered and stored at 4° C. for no longer than 2 weeks. Just before combining with the cells used for conditioning, human bFGF can be added to a final concentration of 4 ng/mL.

The media/medium is then combined with the cells used for conditioning in an environment that allows the cells to release into the medium the components that support embryonic stem cells. Optionally, the cells can be inactivated (i.e., rendered incapable of substantial replication) by radiation (e.g., about 4,000 rads), treatment with a chemical inactivator like mitomycin c, or by any other effective method. The inactivation of the cells is not necessary in instances where the medium is separated from the conditioning cells before use in supporting stem cell cultures.

The cells are cultured in the medium for sufficient time to allow adequate concentration of released factors (or consumption of media components) to produce a medium that supports the culturing of embryonic stem cells without differentiation. Typically, medium conditioned by culturing for 24 h at 37° C. produces medium that supports embryonic stem cell culture for 24 hours. However, the culturing period can be adjusted upwards or downwards, determining empirically (or by assaying for the concentration of essential factors) what constitutes an adequate period. After collecting a batch of conditioned medium, the cells can be used to condition a further batch of medium over a further culture period, for as many cycles as desired as long as the cells retain their ability to condition the medium in an adequate fashion. For example, fibroblast-like cells derived from differentiation of embryonic stem cells can be used to condition medium over 1-day periods for 1-2 weeks.

Mouse embryonic fibroblasts (mEF) can be used to condition media. mEF cells can be obtained from outbred CF1 mice (SASCO) or other suitable strains. In an illustrative method, the abdomen of a mouse at 13 days of pregnancy is swabbed with 70% ethanol, and the decidua is removed into phosphate buffered saline (PBS). Embryos are harvested; placenta, membranes, and soft tissues are removed; and the carcasses are washed twice in PBS. They are then transferred to fresh 10 cm bacterial dishes containing 2 mL trypsin/EDTA, and finely minced. After incubating 5 min at 37° C., the trypsin is inactivated with 5 mL DMEM containing 10% FBS, and the mixture is transferred to a 15 mL conical tube. Debris is allowed to settle for 2 min, the supernatant is made up to a final volume of 10 mL, and plated onto a 10 cm tissue culture plate or T75 flask. The flask is incubated undisturbed for 24 h, after which the medium is replaced. When flasks are confluent (.about.2-3 d), they are split 1:2 into new flasks. Mouse embryonic fibroblasts can be propagated in mEF medium, containing 90% DMEM (Gibco #11965-092), 10% FBS (Hyclone #30071-03), and 2 mM L-glutamine. T150 flasks are used (Corning #430825), splitting the cells 1:2 every other day with trypsin, to keep the cells sub-confluent.

The embryonic stem cells can be plated onto the container in a suitable distribution and in the presence of the conditioned medium. The propagation of mouse embryonic stem cells involves dispersing the cells into a single-cell suspension (Robinson, Meth. Mol. Biol. 75:173, 1997 at page 177). In contrast, the passage of primate embryonic stem cells in the absence of feeders benefits from preparing the primate embryonic stem cells in small clusters.

A convenient way to determine whether embryonic stem cells are differentiating is to follow the morphological features of the colonies. For example, characteristic morphological features of undifferentiated hES cells are known by those skilled in the art, and include high nuclear/cytoplasmic ratios, prominent nucleoli, and compact colony formation with poorly discernable cell junctions. During passage, some cells may differentiate (particularly when replated as single cells, or when large clusters are allowed to form). However, cultures typically reestablish a larger proportion of undifferentiated cells during the culture period. Ideally, the propagated cells will have a doubling time of no more than about 20-40 hours.

Pluripotent stem cells propagated according to the invention may achieve approximately fifty (50) population doublings in approximately seventy (70) days.

The cell culture apparatus of the present invention can be used to test various inhibitors or stimulators to determine their effectiveness in a cell study. Stimulators can include growth factors, which are known in the art. For example, these can include one or more of platelet derived growth factors (PDGF), e.g., PDGF AA, PDGF BB; insulin-like growth factors (IGF), e.g., IGF-I, IGF-II; fibroblast growth factors (FGF), e.g., acidic FGF, basic FGF, β-endothelial cell growth factor, FGF 4, FGF 5, FGF 6, FGF 7, FGF 8, and FGF 9; transforming growth factors (TGF), e.g., TGF-P1, TGF β1.2, TGF-β2, TGF-β3, TGF-β5; bone morphogenic proteins (BMP), e.g., BMP 1, BMP 2, BMP 3, BMP 4; vascular endothelial growth factors (VEGF), e.g., VEGF, placenta growth factor; epidermal growth factors (EGF), e.g., EGF, amphiregulin, betacellulin, heparin binding EGF; interleukins, e.g., IL-1, IL-2, IL-3, IL-4, IL-5, IL-6, IL-7, IL-8, IL-9, IL-10, IL-11, IL-12, IL-13, IL-14; colony stimulating factors (CSF), e.g., CSF-G, CSF-GM, CSF-M; nerve growth factor (NGF); stem cell factor; hepatocyte growth factor, and ciliary neurotrophic factor. Additional growth factors are described in Sporn and Roberts, *Peptide Growth Factors and Their Receptors I*, Springer-Verlag, New York (1990), which is hereby incorporated by reference. The term "growth factors" is intended to encompass presently unknown growth factors that may be discovered in the future, since their characterization as a growth factor will be readily determinable by persons skilled in the art.

Many growth factors are available commercially from vendors, such as Sigma Chemical Co., St. Louis, Mo.; Collaborative Research, Los Altos, Calif.; Genzyme, Cambridge, Mass.; Boehringer, Germany; R&D Systems, Minneapolis, Minn.; Genetech, San Francisco, Calif.; and GIBCO, Grand Island, N.Y. The commercially available growth factors may be obtained in both natural and recombinant forms.

Therefore, in various embodiments, the present invention provides for the stable, consistent propagation of pluripotent embryonic stem cells in a substantially undifferentiated state without utilizing a feeder layer to support the growth of the cells. Those and other embodiments, aspects, objects, and features of the invention will become apparent from the following detailed description of the exemplary embodiments, read in conjunction with, and reference to, the accompanying figures. The following examples are for illustrative purposes and are not intended to, in any way, limit the embodiments and uses of the present invention.

EXAMPLES

Example 1

Optimization of ECM-Coated Surfaces

In an effort to prepare stable, ready-to-use ECM-coated substrates, BD Matrigel™ Matrix (Cat. No. 354234; Becton, Dickinson & Co.) was first thawed overnight at 4° C. on ice. A series of dilutions of Matrigel™ (10 mg/ml stock) was then prepared (e.g., 1:30, 1:100, 1:300, 1:3000, 1:30,000) using cold (4° C.) DMEM (Cat. No. 10313-021; Invitrogen) or K/O-DMEM (Cat. No. 10829-018; Invitrogen). Aliquots (2 mls/well) of each of the five diluted Matrigel solutions and a control solution were added to the wells of a 6-well plate (Cat. No. 353046; Becton, Dickinson & Co.), swirled gently to coat the entire bottom surface of the well, and incubated at room temperature for about two hours. Each 6-well plate included at least one control well, which received the control solution. The control solution was media with no Matrigel™.

After incubation, the Matrigel™ dilutions and the control solution were removed from the wells via aspiration, and 6 mls of ddH$_2$O was added in order to wash the wells and remove unbound material. Within about five minutes of adding the wash solution, it was removed via aspiration, and the plates were dried overnight in a drying oven at room temperature with the lids on for at least about 16 hours. After the drying cycle, the plates were removed from the oven, and passed through a UV tunnel for sterilization. Thereafter, the sterilized plates were individually packaged in moisture-resistant vacuum seal foil bags, and stored promptly at −20° C.

Results obtained via culturing of hES cells on the plates coated with the Matrigel™ dilutions are summarized below in Example 6. These results indicated that suitable coatings included those deposited from a coating solution, wherein the total protein concentration in the coating solution was from about 10 µg/ml to about 1 mg/ml. In some embodiments, the total protein concentration in the coating solution was about 30 µg/ml to about 300 µg/ml. In other preferred embodiments, the total protein concentration in the coating solution was about 30 µg/ml to about 200 µg/ml. The performance of the coated surfaces was defined by the number of colonies and the lack of cell differentiation markers and the presence of undifferentiated markers.

ECM-coating solutions including a mixture of laminin/entactin or laminin/collagen IV may be prepared by diluting a stock concentration of the ECM mixture to a final total protein concentration of about 30 µg/ml to about 300 µg/ml in media or other suitable aqueous solvent. The coating procedure is the same as that described above for the Matrigel™ dilutions. Sample results obtained via culturing of hES cells on plates coated with mixtures of laminin/entactin are summarized below in Example 6. These results indicated that the laminin/entactin-coated surfaces performed as well as test surfaces coated with the Matrigel™ dilutions and feeder cell control surfaces.

Figure 2:
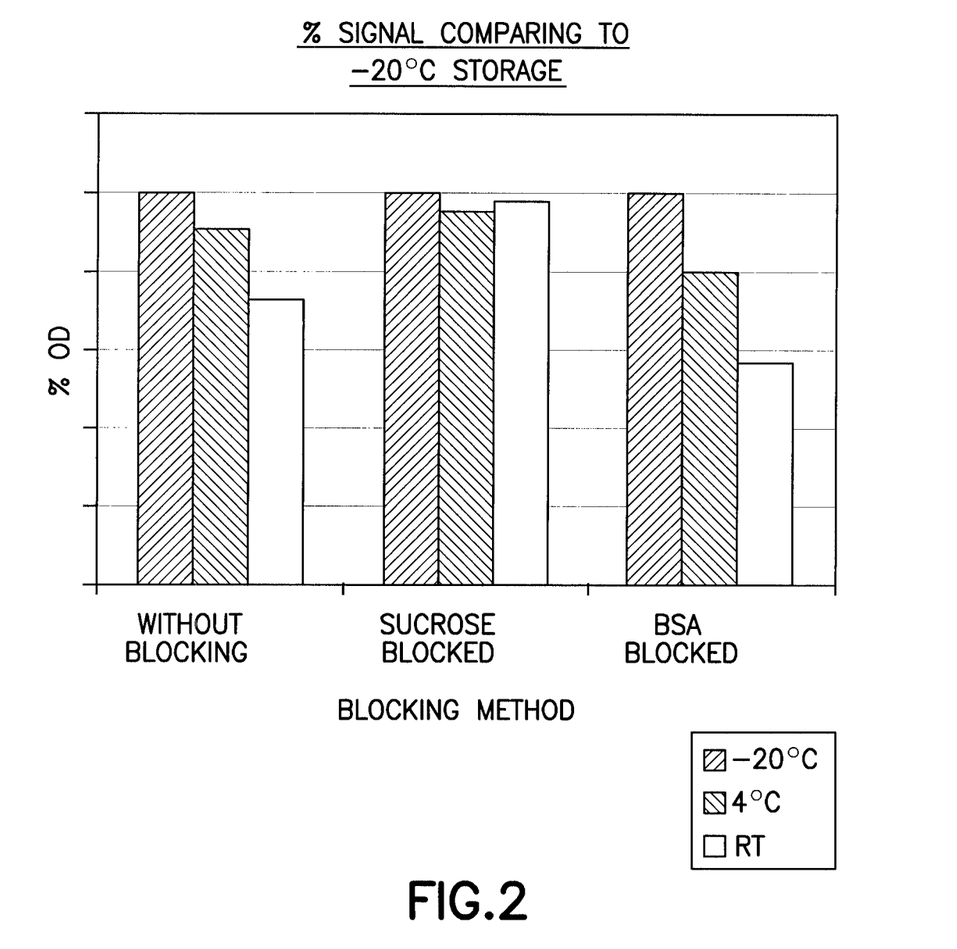
FIG. 2 is a bar graph comparing the % OD signal (y-axis) obtained under different blocking conditions and temperatures for an ECM-coated surface of the present invention. For each of the conditions shown on the x-axis, the first, second and third bars (left to right) represent the signals obtained at −20° C., 4° C. and room temperature, respectively. In this experiment, sucrose was present in the blocking composition at a concentration of 1.25% w/v.

It is noted that, optionally, the aforementioned washing step used to prepare the cell culture products of the invention may be performed with a blocking solution, whereby the wells are effectively both washed and blocked at the same time. The present inventors have found, for example, that blocking of the well surface with a blocking solution including at least one blocking agent, such as sucrose, increased the stability of the surface during an accelerated aging test at higher temperatures. In particular, it was found that sucrose-blocked wells stored at room temperature or 4° C. produced an increase in the signal dynamic range over that obtained without blocking at similar temperatures. This is shown, for example, in FIG. 2, where the sucrose was present in the blocking solution at 1.25% w/v. In some embodiments, the sucrose was present in the blocking solution in amounts of about 0.1 to 5% w/v. It is also well within the contemplation of the present invention that other sugars, such as trehalose, or proteins, such as gelatin, would be useful in this regard.

The performance of the coated surfaces was further defined by the results of an ELISA assay for a major ECM component. These results are described below in Example 2.

Example 2

Determination of Amount of Absorbed Protein on Coated Plates

The present example is directed to the detection and quantitation of extracellular matrix protein adsorbed to the coated surface using an ELISA assay. The ELISA assay was designed to detect collagen IV in the plate coating, using an anti-mouse collagen IV antibody. Collagen IV is a major ECM component. Detection of other proteins in the plate coating is also possible and well within the ability of the skilled artisan through the use of antibodies specific for other proteins in the coating composition.

Plates coated as described in Example 1 (100 µg/mL) and uncoated control plates were allowed to equilibrate to room temperature. Coated plates were washed by adding 2 mL wash buffer (0.2 mL Tween-20 (Sigma-Aldrich, St. Louis, Mo., Product #1379) in 1 L of 1×PBS (without calcium and magnesium ions)) to each well, removing the wash buffer and blotting each plate on paper towels to remove excess liquid on the sides of the wells. The wash procedure was repeated two additional times. 1 mL of blocking solution (1:20 (v/v) dilution of KPL 10% BSA Diluent/Blocking buffer (Cat. No. 50-61-10) in 1× Dulbecco's PBS) was added to each well and the plates were incubated at room temperature for one hour. At the end of the incubation period, the blocking solution was removed from the plates and the wash procedure was repeated three times.

Anti-mouse collagen IV primary antibody working solution was added to each well (1 ml/well). The primary antibody working solution was prepared as a 1:80 (v/v) dilution of a stock antibody solution (0.5 mL stock into 40 mL blocking solution). The stock antibody solution (approximately 1:100 dilution) was prepared by diluting rabbit anti-mouse collagen IV antibody (Chemicon Cat. #AB756P) into blocking solution (above). New lots of anti-mouse collagen IV antibody were qualified by comparing dose response curves made with various dilutions of the new antibody lot with the same dilutions of the first antibody lot. Equivalent dilutions of the new antibody lot were determined by examining the linear region of the dose response curve. After adding the primary antibody working solution, the plates were incubated for 2 hours at room temperature. At the end of the incubation period, the primary antibody working solution was removed from the plates and the wash procedure was repeated three times.

A working solution of goat anti-rabbit IgG secondary antibody conjugated to horseradish peroxidase (HRP) was added to each well (1 ml/well). The secondary antibody working solution was prepared by preparing a 1:100 (v/v) dilution of a stock antibody solution (0.4 mL stock into 40 mL blocking solution). The stock antibody solution (approximately 1:100 dilution) was prepared by diluting the secondary antibody (BD Pharmingen, Cat. #554021) in blocking solution (above). New lots of secondary antibody were qualified by comparing dose response curves made with various dilutions of the new antibody lot with the same dilutions of the first antibody lot. Equivalent dilutions of the new antibody lot were determined by examining the linear region of the dose response curve. After adding the secondary antibody working solution, the plates were incubated for 1 hour at room temperature. At the end of the incubation period, the secondary antibody working solution was removed from the plates and the wash procedure was repeated three times.

After equilibrating to room temperature, 1 mL of the horseradish peroxidase substrate tetramethylbenzidine (TMB) (SureBlue Reserve (1-Component) TMB Microwell Peroxidase (KPL, Inc., Cat. #53-00-02) was added to each well. The plates were incubated at room temperature for 8 minutes to allow the color to develop. After 8 minutes, 1 mL of an acidic stop solution (TMB stop solution from KPL, Inc. Cat #50-85-05) was added to each well. 200 µL of the reaction mixture from each well was transferred to a 96-well plate and the absorbance measured at 450 nm at room temperature (Spectramax Plus plate reader). The plates were read within 5 minutes after stopping the reaction. The average O.D. reading for wells containing the same reaction mixture was calculated. The background was calculated by dividing the average O.D. of the sample wells by the mean O.D. of the uncoated control wells.

Figure 1:
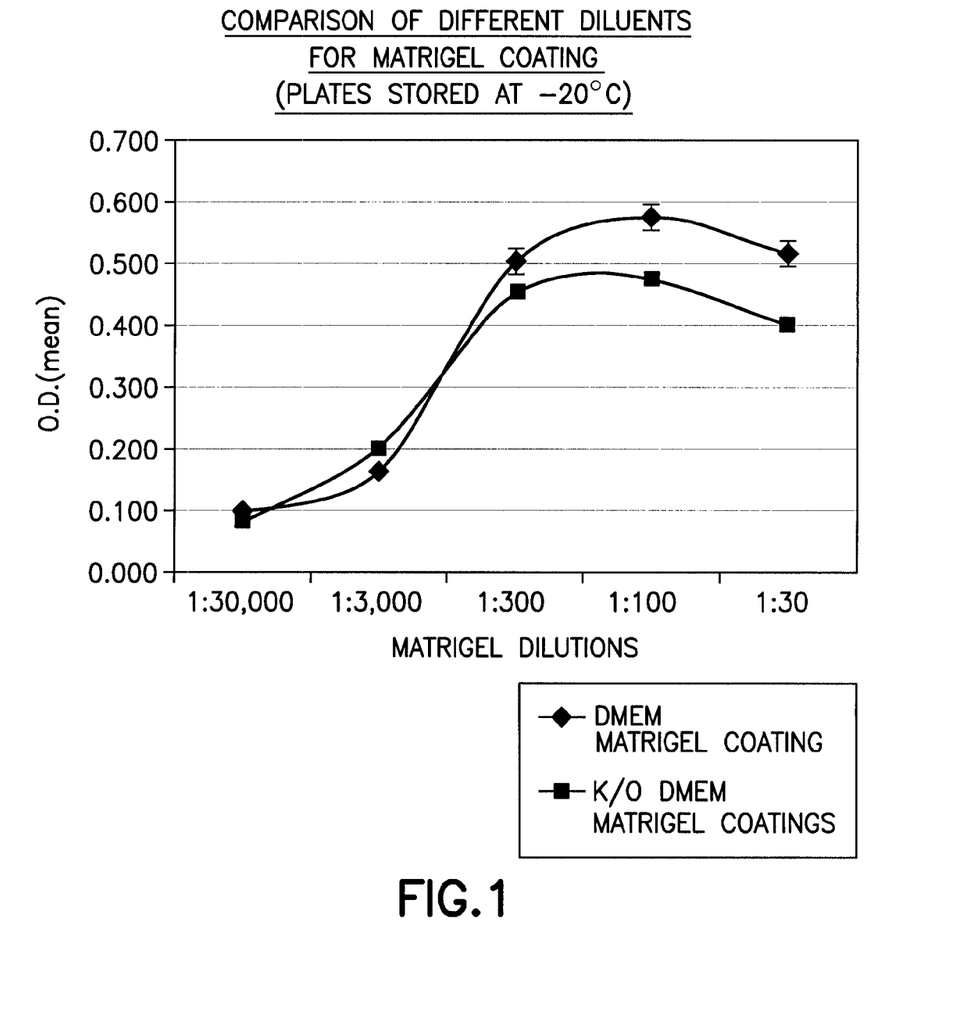
FIG. 1 is a graph of collagen IV ELISA data. The graph compares the absorbance signal obtained from different ECM-coated surfaces.

The wells of the coated plates had an optical density of at least about 0.5 using the reagents and methods described in the present example. These results are depicted in FIG. 1. The ratio of the optical densities of the wells of the coated plates to the uncoated plates was greater than about 4.0.

Example 3

Preparation of Fibroblast (MEF) Feeder Layers

The present example is directed to the procedure used to prepare MEF feeder layers from which MEF-conditioned medium was harvested. Moreover, MEF feeder layers were used as a control surface for culturing human embryonic stem cells according to methods well known in the art.
Preparation of Substratum For Feeder Cells Inactivated MEF feeder cells (irradiated or mitomycin-C treated CF-1 line from ATCC, Manassas, Va.) are seeded on gelatinized cell culture dishes in order to provide better support for long culture periods. In particular, culture dishes are coated with a 0.1% gelatin solution, followed by incubation for about 1 hour to overnight at room temperature. Thereafter, the gelatin was removed, and the gelatin-coated dishes were rinsed with calcium, magnesium free Phosphate Buffered Saline (PBS) just prior to plating the inactivated feeder cells thereon.
Thawing and Culturing of the Feeder Cells A vial of cells (irradiated MEFs from CF-1; Catalog No. SCRC 1040.1 from ATTCC) was first thawed by gently shaking it in a 37° C. water bath. As soon as the cells were thawed, the vial was removed from the water bath, and the outside of the vial was treated with 70% ethanol. Then, the vial was moved to a tissue culture hood, where the remaining steps of the procedure were performed aseptically. The cell contents of the vial were aseptically transferred to 10 mls of prewarmed MEF media. Subsequently, the cells were spun at 1000 rpm, and the supernatant was discarded. The cell pellet was resuspended in 48 mls of MEF media and 2.5 mls of this cell suspension were dispensed per well of gelatinized 6-well plates prepared as described above. The plates were then incubated at 5% $CO_2$ in humidified air at 37° C. Approximately 24 hours later, the medium in each of the wells was replaced with 2.5 to 3.0 mls of fibroblast medium or hES media (if the cells were to be used the next day) and the plates were returned to the incubator.

Example 4

Feeder-Free Culturing of Human Embryonic Stem Cells

The present example is directed to the culturing of human embryonic stem (hES) cells on an ECM-coated surface prepared as described in Example 1 above. The hES cells are cultured in the presence of MEF-conditioned medium, the preparation of which is described below. It is noted, however, that the culturing method of the present invention is not limited to this medium, as prior studies have established that embryonic stem cells can be successfully cultured on ECM surfaces using different conditioned and defined media herein described.

Preparation of MEF-Conditioned Medium

MEF feeder cells are cultured and inactivated as described above in Example 3. MEF feeder cells were plated at 56,000 cells/$cm^2$ in MEF medium. The following volumes were used: 3 ml/well for a 6-well plate; 10 ml for a 75 ml tissue culture flask; and 20 ml for a 150 ml tissue culture flask. The MEFs were cultured overnight. The medium on the MEFs was replaced with hES cell medium supplemented with 4-10 ng/ml hbFGF the night before harvest of the conditioned medium. Conditioned medium from feeder plates or flasks was collected after overnight incubation of the MEFs in the hES medium. Fresh hESC medium containing 4-10 ng/ml hbFGF was added to the MEFs, and the above process of culturing the cells overnight, followed by collecting the conditioned medium was repeated. It was found that the MEFs could be used for about 7 days with once daily collection of conditioned medium. Prior to use in culturing hES cells, an additional 8 ng/ml of hbFGF was added to the conditioned medium.
Culturing hES Cells Using MEF-Conditioned Medium on ECM-Coated Surfaces ECM-coated plates prepared as in Example 1 were thawed at room temperature. Then, 2 ml of MEF-Conditioned medium supplemented with 8 ng/ml of hbFGF were added to each well of the 6-well plate, and the plate was placed in a $CO_2$ incubator for up to 2 hours. After optionally hydrating the plate in this way, 0.5 ml of hES cell suspension in MEF-conditioned medium supplemented with 8 ng/ml of hbFGF (Becton, Dickinson & Co.) was added to each well, and the plate was placed back in the $CO_2$ incubator for overnight incubation at 37° C. This corresponded to Day 0. On Day 3, the medium is replaced with fresh medium. Thereafter, the medium is replaced with fresh medium daily up to Day 7. Colonies of hES cells were observable under a microscope. These hES cells could then either be passaged, or employed in immunocytochemistry studies to test for differentiated and undifferentiated hES cells, as described below in Example 5.

Example 5

Immunocytochemistry Protocols

The present example is directed to an immunocytochemistry protocol used to test for differentiated and undifferentiated hES cells. In particular, hES marker antibodies from R&D Systems (cat #SC008) were used to determine the differentiation status of the propagated hES cells from Example 4. The present protocol is for cells grown in a 6-well tissue culture plate.

Cultured hES cells from Example 4 were washed with 2 ml of PBS. Then, the cells were fixed with 1 ml of 4% paraformaldehyde for 20 minutes at room temperature. The fixed cells were washed twice with 2 ml of PBS for 5 minutes each wash. Subsequently, the cells were blocked with 1 ml of 0.1% BSA, 10% normal goat serum. During the blocking, the primary antibody working solution was prepared with PBS containing 1% BSA and 10% normal goat serum to a final desired antibody concentration based on the manufacturer's recommendations. It is noted that, for both the blocking solution, and the primary antibody solution, the normal serum may be replaced with that from another species depending on the host species of the secondary antibody.

After blocking, the cells were incubated with 1 ml/well of the diluted antibody working solution for overnight at 2-8° C. Then, the cells were washed three times with 2 ml of PBS containing 1% BSA for 5 minutes each wash.

The secondary antibody was diluted in PBS containing 1% BSA. Useful fluorescent secondary antibodies included Alex 488 or 594-conjugated appropriate secondary antibodies (Invitrogen-Molecular Probes). These secondary antibodies were used in accordance with the manufacturer's recommendations. The cells were incubated with the secondary antibody at 1 ml/well for 60 minutes at room temperature in the dark. Subsequently, the cells were washed three times with 2 ml of PBS containing 1% BSA for 5 minutes each wash. The cells were thereafter covered with 2 ml of PBS and visualized with a fluorescent microscope.

These immunocytochemistry results are described in Example 6 and summarized in Table 1 below.

Example 6

Results

The culturing system prepared as described in Example 1 above was used to culture hES cells in MEF-CM. However, the method of culturing is not limited to this culture medium. Culturing success depends, at least in part, on methods used for ES cell derivation, dissociation and cryopreservation. Moreover, culturing methods that have been validated over long periods of time, such as those of the present invention, are preferred.

The present inventors have optimized a culturing method using BD BioCoat Matrigel™-coated 6-well plates, as well as 6-well plates coated with a mixture of laminin/entactin, for example. However, these are exemplary coatings, and the present invention is not limited to these as described herein. The culturing method employs pre-qualified reagents, such as BD™ human bFGF as a media supplement and BD™ Dispase for disassociating hES colonies.

Using this method, H9 and/or H1 cell lines from WiCell have been cultured on the optimized BD BioCoat™ Matrigel™ surface for over 40 population doublings with MEF-CM supplemented with 8 ng/ml bFGF. Microscopic images showed that these hES cells typically spread out more on the BioCoat™ Matrigel™ surface and formed larger colonies compared to those cultured on MEF feeders (data not shown).

Cells grown on the newly optimized BioCoat™ Matrigel™ surface stained positive for expression of well characterized undifferentiated markers, Oct-3/4 and SSEA-4, and negative for the differentiated marker, SSEA1. Similar cellular morphologies were obtained from hES cells cultured on the laminin/entactin surfaces, and the cells stained negative for the differentiated cell marker, SSEA1. The results are summarized in Table 1 below.

TABLE 1

|  | Matrigel | Laminin/Entactin |
| --- | --- | --- |
| Colony formation | Yes | yes |
| *Oct 3/4 | positive | positive |
| *SSEA 4 | positive | not tested |
| **SSEA 1 | negative | negative |

*Undifferentiated cell marker;
**Differentiated cell marker

Cellular morphology was comparable to colonies cultured on freshly coated BD Matrigel™ plates and consistent with previous reports (Xu et al. (2001) Nature Biotechnology 9: 971-974; Carpenter et al. (2004) Developmental Dynamics 229: 243-258). H9 cells cultured continuously on the new BD BioCoat™ Matrigel™ surface for 10 passages in media supplemented with FBS without bFGF retained their ability to form embryoid bodies based on microscopic images, suggesting that the ability of these cells to differentiate has not been altered. Preliminary data suggest that this surface will likely be compatible with a number of media described herein that has worked successfully with BD Matrigel™, and that this surface may also be used to culture other ES cells, as suggested by Greenlee et al. in 2005 (Toxicology In Vitro 19: 389-397).

What is claimed is:

1. A cell culture product comprising:
   a substrate; and
   a coating thereon;
   wherein the coating is produced by a method comprising:
   applying a coating solution to the substrate, wherein the coating solution comprises a mixture of extracellular matrix proteins including laminin and at least one other extracellular matrix component and an aqueous solvent, wherein the total protein concentration in the coating solution is about 10 µg/ml to about 1 mg/ml;
   incubating the coating solution on the substrate; and then washing the substrate to remove unbound extracellular matrix proteins.

2. The cell culture product of claim 1, wherein the coating is present on the substrate in a dried state.

3. The cell culture product of claim 1, wherein the total protein concentration in the coating solution is about 30 µg/ml to about 300 µg/ml.

4. The cell culture product of claim 1, wherein the total protein concentration in the coating solution is about 30 µg/ml to about 200 µg/ml.

5. The cell culture product of claim 1, wherein the at least one other extracellular matrix component is entactin.

6. The cell culture product of claim 5, wherein the coating further comprises a component selected from the group consisting of type IV collagen, heparan sulfate proteoglycans (HSPG), growth factors and combinations thereof.

7. The cell culture product of claim 1, wherein the aqueous solvent is a buffer or cell culture media.

8. The cell culture product of claim 1, wherein the coating on the substrate further comprises a blocking composition comprising at least one blocking agent and an aqueous solvent.

9. The cell culture product of claim 8, wherein the blocking agent is selected from the group consisting of gelatin, sucrose and trehalose.

10. The cell culture product of claim 8, wherein the blocking agent is present in the blocking composition in an amount of about 0.1 to about 5.0% w/v.

11. A cell culture product comprising:
    a substrate; and
    an extracellular matrix coating thereon, wherein the coating is provided to at least one surface of the substrate in a solution at a minimal concentration sufficient to saturate the substrate surface with extracellular matrix proteins; and then the substrate is washed to remove unbound extracellular matrix proteins.

12. The cell culture product of claim 11, wherein the total amount of extracellular matrix protein adsorbed by or bound the substrate surface is from about 200 $ng/cm^2$ to about 650 $ng/cm^2$.

13. An apparatus for propagating pluripotent embryonic stem cells comprising:
    a) a container suitable for culturing cells; and
    b) an extracellular matrix in a fixed concentration on at least one surface of the container;
    wherein said extracellular matrix comprises a mixture of laminin and at least one other extracellular matrix component, and
    wherein the extracellular matrix is provided to the at least one surface by coating at least one surface of the container with the extracellular matrix, washing the surface coated with extracellular matrix to remove unbound extracellular matrix proteins, and then drying the container such that the extracellular matrix is in a dried state on at least one surface of said container.

14. The apparatus of claim 13, wherein the extracellular matrix comprises a mixture of laminin and entactin.

* * * * *